United States Patent
Komaki et al.

(10) Patent No.: US 8,090,143 B2
(45) Date of Patent: Jan. 3, 2012

(54) METHOD OF INSPECTING OUTER WALL OF HONEYCOMB STRUCTURE BODY

(75) Inventors: Takeshi Komaki, Nagoya (JP); Tadayoshi Yasui, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 734 days.

(21) Appl. No.: 12/207,171

(22) Filed: Sep. 9, 2008

(65) Prior Publication Data
US 2009/0010523 A1 Jan. 8, 2009

Related U.S. Application Data

(63) Continuation of application No. PCT/JP2007/055456, filed on Mar. 16, 2007.

(30) Foreign Application Priority Data
Mar. 16, 2006 (JP) .................. 2006-072396

(51) Int. Cl.
*G06K 9/00* (2006.01)
(52) U.S. Cl. ...................... 382/100; 382/141
(58) Field of Classification Search .......... 382/100, 382/141–150
See application file for complete search history.

(56) References Cited

U.S. PATENT DOCUMENTS

| | | | |
|---|---|---|---|
| 4,319,840 A * | 3/1982 | Kondo et al. | 356/241.1 |
| 5,548,400 A * | 8/1996 | Bourguinat | 356/241.1 |
| 5,629,067 A * | 5/1997 | Kotani et al. | 428/116 |
| 7,283,224 B1 * | 10/2007 | Smithgall | 356/237.1 |
| 7,727,613 B2 * | 6/2010 | Suwabe et al. | 428/116 |
| 2003/0081202 A1 * | 5/2003 | Yoneda | 356/237.6 |
| 2003/0174320 A1 * | 9/2003 | Yokoyama et al. | 356/237.6 |
| 2006/0119842 A1 | 6/2006 | Gerard et al. | |

FOREIGN PATENT DOCUMENTS

| | | |
|---|---|---|
| CN | 1708684 A | 12/2005 |
| EP | 0 548 695 A2 | 6/1993 |
| EP | 1 271 134 | 1/2003 |
| JP | A 1-165940 | 6/1989 |
| JP | A 5-107197 | 4/1993 |
| JP | A 5-264459 | 10/1993 |
| JP | A 6-51091 | 2/1994 |

OTHER PUBLICATIONS

European Search Report issued in European Patent Application No. 07738901.3 dated Sep. 15, 2010.

* cited by examiner

*Primary Examiner* — Manav Seth
(74) *Attorney, Agent, or Firm* — Oliff & Berridge, PLC

(57) ABSTRACT

There is disclosed a method of inspecting the outer wall of a honeycomb structure body which can be performed without relying on human sensory functions and in which a defect detection level and an inspection time per honeycomb structure body are constant, so that stable inspection can be performed. In a method of inspecting the outer wall of a honeycomb structure body 1 made of a ceramic material, while rotating the honeycomb structure body 1, the outer wall of the honeycomb structure body 1 is imaged by a line camera 2, and the thus obtained image is processed to judge whether or not a defect is present in the outer wall of the honeycomb structure body 1.

4 Claims, 1 Drawing Sheet

METHOD OF INSPECTING OUTER WALL OF HONEYCOMB STRUCTURE BODY

TECHNICAL FIELD

The present invention relates to a method of detecting a defect generated in the outer wall of a honeycomb structure body by use of image processing.

BACKGROUND ART

A honeycomb structure body is used as a filter which traps a particulate matter included in an exhaust gas from an internal combustion engine, a boiler or the like, a catalyst carrier of a catalyst for purifying the exhaust gas, or the like. In particular, a honeycomb structure body made of a ceramic material has excellent characteristics such as resistance to heat, resistance to thermal shock and resistance to oxidation, and is broadly used suitably for the above-mentioned application.

In general, the honeycomb structure body made of the ceramic material is manufactured by kneading ceramic powder with an organic binder, water and the like to form clay, forming the clay into a honeycomb shape by an extrusion forming process or the like, subjecting the resultant material to drying, calcining and the like if necessary, and then firing the material. However, in such manufacturing steps, various defects (cut, hole, crack, attachment of dust, dirt, uneven surface, scratch, mixing of foreign matters, and the like) are generated sometimes in the outer wall of the honeycomb structure body.

Such defects of the outer wall deteriorate the strength of the honeycomb structure body, a filtering performance in a case where the honeycomb structure body is used as the filter, an exhaust gas purification performance in a case where the honeycomb structure body is used as the catalyst carrier, and the like. Therefore, the presence of the defect in each of manufactured honeycomb structure bodies needs to be inspected. Heretofore, such an inspection of the defect generated in the outer wall of the honeycomb structure body has been performed by a visual inspection (any prior art document concerning such a conventional technology is not especially found).

However, such a visual inspection is a sensory inspection based on a human visual sense, and hence the defect is missed in not a few cases. Moreover, fluctuation is generated in a defect detection level owing to a difference in a visual power or a fatigue degree, and it is difficult to perform stable inspection. Furthermore, fluctuation is generated in an inspection time per honeycomb structure body owing to the difference in the fatigue degree or a product dimension, and it is therefore difficult to perform the efficient and stable industrial production of the honeycomb structure body. In addition, when the defect detection level has to be raised, the number of inspecting persons has to be increased, and the inspection time per honeycomb structure body has to be lengthened, so that productivity deteriorates.

DISCLOSURE OF THE INVENTION

The present invention has been developed in view of such a problem of a conventional technology, and an object thereof is to provide a method of inspecting the outer wall of a honeycomb structure body which can be performed without relying on human sensory functions and in which a defect detection level and an inspection time per honeycomb structure body are constant, so that stable inspection can be performed.

To achieve the above object, according to the present invention, the following method of inspecting a defect in the outer wall of the honeycomb structure body is provided.

[1] A method of inspecting the outer wall of a honeycomb structure body made of a ceramic material, comprising: imaging the outer wall of the honeycomb structure body by a line camera while rotating the honeycomb structure body; and processing the thus obtained image to judge whether or not a defect is present in the outer wall of the honeycomb structure body.

[2] The method of inspecting the outer wall of the honeycomb structure body according to the above [1], wherein the outer wall of the honeycomb structure body is imaged while irradiating the outer wall of the honeycomb structure body with light.

[3] The method of inspecting the outer wall of the honeycomb structure body according to the above [2], wherein in a case where the honeycomb structure body is viewed from the axial direction of the honeycomb structure body, an angle at which the outer wall of the honeycomb structure body is irradiated with the light is 30° or less with respect to an axial line connecting the center of the honeycomb structure body to the line camera.

[4] The method of inspecting the outer wall of the honeycomb structure body according to any one of the above [1] to [3], wherein the eccentricity of the honeycomb structure body during the rotation is within ±1.5 mm.

[5] The method of inspecting the outer wall of the honeycomb structure body according to any one of the above [1] to [4], including a step of binarizing the obtained image; a step of removing noise; and a step of judging whether or not the defect is present.

The method of inspecting the outer wall of the honeycomb structure body according to the present invention can be performed without relying on human sensory functions, and a defect detection level and an inspection time per honeycomb structure body are constant, so that stable inspection can be performed.

DESCRIPTION OF REFERENCE NUMERALS

1: honeycomb structure body, 2: line camera, 3: light

BEST MODE FOR CARRYING OUT THE INVENTION

The best mode for carrying out the present invention will hereinafter be described, but it should be understood that the present invention is not limited to the following embodiment and that the following embodiment subjected to appropriate change, improvement or the like based on the ordinary knowledge of any person skilled in the art without departing from the scope of the present invention falls in the scope of the present invention.

In a method of inspecting the outer wall of a honeycomb structure body according to the present invention, first while rotating the honeycomb structure body as an inspection target, the outer wall of the honeycomb structure body is imaged by a line camera. There is not any special restriction on a method of rotating the honeycomb structure body, but, for example, a method of mounting the honeycomb structure body on a turntable to rotate the honeycomb structure body together with the turntable is preferably simple. It is to be noted that when this honeycomb structure body is rotated, eccentricity during the rotation is preferably within ±1.5 mm. In a case where the eccentricity during the rotation exceeds this range, even when the honeycomb structure body as the inspection target is columnar, that is, the sectional shape of the honeycomb structure body viewed from the axial direction thereof is circular, the focus of the line camera deviates during the imaging, and a part of the obtained image becomes blurred sometimes. In a case where the turntable is used in rotating the honeycomb structure body, the honeycomb structure body is mounted so that the rotary shaft of the turntable matches the central axis of the honeycomb structure body.

It is to be noted that even when the sectional shape of the honeycomb structure body viewed from the axial direction thereof is a shape other than the circular shape, for example, an elliptic shape, a quadrangular shape or the like, the position of the line camera can be moved to adjust the focus of the line camera, thereby imaging the outer wall. Moreover, when the honeycomb structure body is made of a ceramic material, the present invention is applicable to any stage of a manufacturing process, for example, a formed body, a dried body, a calcined body, a sintered body or the like.

Figure 2:
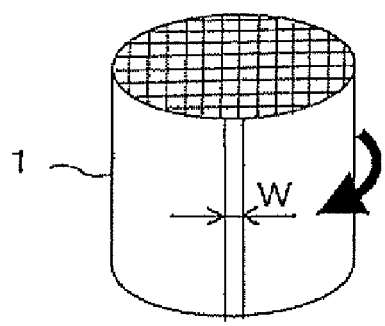
FIG. 2 is a perspective view showing a method of imaging the outer wall of a honeycomb structure body by a line camera.

As shown in FIG. 2, the imaging by the line camera is accomplished by imaging the outer wall of a honeycomb structure body 1 in a predetermined width W every line, and the imaging of the whole outer wall is completed while the honeycomb structure body 1 rotates once. The imaging width W per line is appropriately about 10 to 100 µm, depending on the specifications or the like of the line camera for use. As the line camera for use, a line camera having a driving frequency of about 10 to 100 MHz and including about 2000 to 10000 pixels is preferable.

Figure 1:
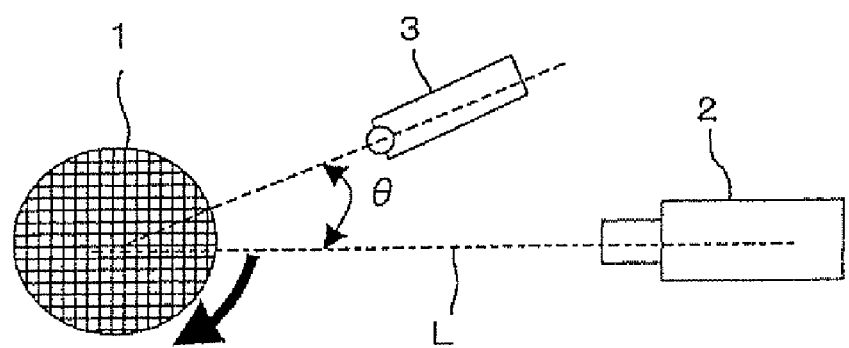
FIG. 1 is an explanatory view showing one example of an embodiment of an inspection method according to the present invention.

As shown in FIG. 1, the imaging is preferably accomplished while irradiating the outer wall of the honeycomb structure body 1 with light by use of a light 3. In consequence, the shade of a defect portion becomes clear, and an image having a high contrast can be obtained. It is to be noted that during the irradiation with this light, in a case where the honeycomb structure body 1 is viewed from the axial direction of the honeycomb structure body, an angle θ at which the outer wall of the honeycomb structure body 1 is irradiated with the light is preferably set to 30° or less with respect to an axial line L connecting the center of the honeycomb structure body 1 to the line camera 2, so that the shade of the defect portion clearly emerge. As the light for irradiating the outer wall with the light, for example, a halogen lamp is preferably usable, and the light of the lamp is preferably condensed by a condensing lens to irradiate the line for imaging the outer wall of the honeycomb structure body.

The thus obtained image of the outer wall of the honeycomb structure body is subjected to image processing, to judge whether or not a defect is present in the outer wall. In the specific procedure of the image processing, it is preferable that the obtained image is first subjected to binarization processing. In a case where this binarization processing is performed, a portion which might be the defect turns black, another portion turns white, and the portion which might be the defect and the shape, the dimension or the like of the portion are clarified.

Moreover, when the defect of the outer wall to be detected is, for example, "cut" or "crack", it is preferable to perform noise removal processing for removing the image of dust, trash or the like considered to be unrelated with the defect by use of a noise removal filter or the like.

From the image of the outer wall subjected to the binarization processing and the noise removal processing, it is judged whether or not the defect is present in the outer wall. Specifically, a threshold value is set, and the defect is automatically distinguished by judging whether or not the length or the like of the black portion which might be the defect is above or below the threshold value. Examples of an item to which the threshold value is set include the length, the width, the aspect ratio, the area and the like of the black portion, and one or more items effective for the detection are appropriately selected from these items in accordance with the type or the like of the defect to be detected. Moreover, as the set value of the threshold value, an effective value is appropriately set in accordance with the type, the demanded detection level or the like of the defect to be detected.

Such image processing and the judgment of the presence of the defect by the processing can be performed using a commercially available image processing system. For example, SmartView as a defect inspection system manufactured by Cognex Co. or the like is preferably usable.

EXAMPLES

The present invention will hereinafter be described in more detail in accordance with examples, but the present invention is not limited to these examples.

Examples 1 to 18

Fifteen sintered honeycomb structure bodies (sample Nos. 1 to 15) made of cordierite which had defects in the outer walls of the bodies or which did not have any defect in the outer walls as shown in Table 1 were prepared, and the outer walls of the honeycomb structure bodies (the sintered bodies) were inspected by an inspection method according to the present invention to judge a detectability and to check a time (tact time) required for the inspection of each of the honeycomb structure bodies. The central axis of the honeycomb structure body as an inspection target was matched with the rotary shaft of a turntable to mount the body on the turntable so that eccentricity during the rotation was within ±1.5 mm. As a line camera, a line camera having a driving frequency of 40 MHz and including 4000 pixels was used. While the turntable was rotated once in three seconds, the outer wall of the honeycomb structure body was imaged in a width of 15 µm every line. The imaging of the whole outer wall was completed while the honeycomb structure body rotated once. Moreover, during this imaging, as a light, a 150 W halogen lamp was used, and the light of the lamp was condensed in a width of 5 mm by a condensing lens to irradiate the line for imaging the outer wall of the honeycomb structure body with the light. As to an irradiation angle, an irradiation angle θ with respect to an axial line L connecting the center of a honeycomb structure body 1 to a line camera 2 as shown in FIG. 1 was set to each of values shown in Table 2. To process the obtained image of the outer wall and to judge the presence of a defect, SmartView manufactured by Cognex Co. was used. Items to which threshold values for judging the presence of the defect were to be set included an aspect ratio (a width/a length), the width, the length, and an area (the width×the length). When all of the items corresponded to the threshold values shown in Table 2, it was judged that the defect was present. The inspection was performed by five inspecting persons (inspecting persons A to E), and the inspection results of the inspecting persons are shown in Table 2. It is to be noted that as to the detectability in the table, in Examples 1 to 15 where the honeycomb structure bodies having the defects (sample Nos. 1 to 12) were inspection targets, the result was "circle" in a case where the defect was detected, and the result was "cross" in a case where any defect was not detected. On the other hand, in Examples 16 to 18 where the honeycomb structure bodies which did not have any defect (sample Nos. 13 to 15) were inspection targets, the result was "circle" in a case where any defect was not detected, and the result was "cross" in a case where the defect was detected owing to wrong judgment.

Comparative Examples 1 to 15

The same honeycomb structure bodies as those used as the inspection targets in Examples 1 to 18 described above were subjected to a conventional human visual outer wall inspection to check a detectability and a time (tact time) required for the inspection of each of the honeycomb structure bodies. The inspection was performed by five inspecting persons (inspecting persons A to E), and the inspection results of the inspecting persons are shown in Table 3. It is to be noted that as to the detectability in the table, in Comparative Examples 1 to 12 where the honeycomb structure bodies having the defects (sample Nos. 1 to 12) were inspection targets, the result was "circle" in a case where the defect was detected, and the result was "cross" in a case where any defect was not detected. On the other hand, in Comparative Examples 13 to 15 where the honeycomb structure bodies which did not have any defect (sample Nos. 13 to 15) were inspection targets, the result was "circle" in a case where any defect was not detected, and the result was "cross" in a case where the defect was detected owing to wrong judgment.

TABLE 1

| Sample No. | Sample shape | Sample dimension (diameter mm × height mm) | Type of defect | Defect dimension (width mm × length mm) |
|---|---|---|---|---|
| 1 | Columnar | 103 × 105 | Cut | 0.02 × 15 |
| 2 | Columnar | 103 × 105 | Cut | 0.03 × 25 |
| 3 | Columnar | 103 × 88 | Cut | 0.03 × 5 |
| 4 | Columnar | 129 × 80 | Cut | 0.02 × 10 |
| 5 | Columnar | 93 × 125 | Cut | 0.02 × 3 |
| 6 | Columnar | 76 × 50 | Cut | 0.02 × 2 |
| 7 | Columnar | 106 × 81 | Cut | 0.03 × 3 |
| 8 | Columnar | 86 × 120 | Cut | 0.1 × 4 |
| 9 | Columnar | 86 × 75 | Cut | 0.02 × 120 |
| 10 | Columnar | 86 × 58 | Dust | 0.05 × 0.5 |
| 11 | Columnar | 118 × 58 | Dust | 1 × 1 |
| 12 | Columnar | 99 × 93 | Uneven surface | 0.05 × 1 |
| 13 | Columnar | 106 × 97 | No defect | — |
| 14 | Columnar | 106 × 114 | No defect | — |
| 15 | Columnar | 106 × 114 | No defect | — |

TABLE 2

| | | Inspection conditions | | | | | Inspection using method of the present invention | | | |
|---|---|---|---|---|---|---|---|---|---|---|
| | | | Threshold values | | | | | | | |
| | | Irradiation | Aspect ratio | | | | Inspecting person A | | Inspecting person B | |
| Example No. | Sample No. | angle (deg) | (width/length) | Width (mm) | Length (mm) | Area (mm$^2$) | Detectability | Tact (seconds) | Detectability | Tact (seconds) |
| 1 | 1 | 5 | 0.2 or less | 0.01 or more | 0.3 or more | 0.01 or more | ○ | 3 | ○ | 3 |
| 2 | 2 | 5 | 0.2 or less | 0.01 or more | 0.3 or more | 0.01 or more | ○ | 3 | ○ | 3 |
| 3 | 2 | 10 | 0.2 or less | 0.01 or more | 0.3 or more | 0.01 or more | ○ | 3 | ○ | 3 |
| 4 | 2 | 20 | 0.2 or less | 0.01 or more | 0.3 or more | 0.01 or more | ○ | 3 | ○ | 3 |
| 5 | 2 | 30 | 0.2 or less | 0.01 or more | 0.3 or more | 0.01 or more | ○ | 3 | ○ | 3 |
| 6 | 3 | 10 | 0.2 or less | 0.01 or more | 0.3 or more | 0.01 or more | ○ | 3 | ○ | 3 |
| 7 | 4 | 10 | 0.2 or less | 0.01 or more | 0.3 or more | 0.01 or more | ○ | 3 | ○ | 3 |
| 8 | 5 | 10 | 0.2 or less | 0.01 or more | 0.3 or more | 0.01 or more | ○ | 3 | ○ | 3 |
| 9 | 6 | 10 | 0.2 or less | 0.01 or more | 0.3 or more | 0.01 or more | ○ | 3 | ○ | 3 |
| 10 | 7 | 10 | 0.2 or less | 0.01 or more | 0.3 or more | 0.01 or more | ○ | 3 | ○ | 3 |
| 11 | 8 | 10 | 0.2 or less | 0.01 or more | 0.3 or more | 0.01 or more | ○ | 3 | ○ | 3 |
| 12 | 9 | 10 | 0.2 or less | 0.01 or more | 0.3 or more | 0.01 or more | ○ | 3 | ○ | 3 |
| 13 | 10 | 10 | 0.2 or less | 0.01 or more | 0.3 or more | 0.01 or more | ○ | 3 | ○ | 3 |
| 14 | 11 | 10 | 0.2 or less | 0.01 or more | 0.3 or more | 0.01 or more | ○ | 3 | ○ | 3 |
| 15 | 12 | 10 | 0.2 or less | 0.01 or more | 0.3 or more | 0.01 or more | ○ | 3 | ○ | 3 |
| 16 | 13 | 10 | 0.2 or less | 0.01 or more | 0.3 or more | 0.01 or more | ○ | 3 | ○ | 3 |
| 17 | 14 | 10 | 0.2 or less | 0.01 or more | 0.3 or more | 0.01 or more | ○ | 3 | ○ | 3 |
| 18 | 15 | 10 | 0.2 or less | 0.01 or more | 0.3 or more | 0.01 or more | ○ | 3 | ○ | 3 |

TABLE 2-continued

| | Inspection using method of the present invention | | | | | | |
|---|---|---|---|---|---|---|---|
| | Inspecting person C | | Inspecting person D | | Inspecting person E | | Detection | Average |
| Example No. | Detectability | Tact (seconds) | Detectability | Tact (seconds) | Detectability | Tact (seconds) | ratio (%) | tact (seconds) |
| 1 | ○ | 3 | ○ | 3 | ○ | 3 | 100 | 3 |
| 2 | ○ | 3 | ○ | 3 | ○ | 3 | 100 | 3 |
| 3 | ○ | 3 | ○ | 3 | ○ | 3 | 100 | 3 |
| 4 | ○ | 3 | ○ | 3 | ○ | 3 | 100 | 3 |
| 5 | ○ | 3 | ○ | 3 | ○ | 3 | 100 | 3 |
| 6 | ○ | 3 | ○ | 3 | ○ | 3 | 100 | 3 |
| 7 | ○ | 3 | ○ | 3 | ○ | 3 | 100 | 3 |
| 8 | ○ | 3 | ○ | 3 | ○ | 3 | 100 | 3 |
| 9 | ○ | 3 | ○ | 3 | ○ | 3 | 100 | 3 |
| 10 | ○ | 3 | ○ | 3 | ○ | 3 | 100 | 3 |
| 11 | ○ | 3 | ○ | 3 | ○ | 3 | 100 | 3 |
| 12 | ○ | 3 | ○ | 3 | ○ | 3 | 100 | 3 |
| 13 | ○ | 3 | ○ | 3 | ○ | 3 | 100 | 3 |
| 14 | ○ | 3 | ○ | 3 | ○ | 3 | 100 | 3 |
| 15 | ○ | 3 | ○ | 3 | ○ | 3 | 100 | 3 |
| 16 | ○ | 3 | ○ | 3 | ○ | 3 | 100 | 3 |
| 17 | ○ | 3 | ○ | 3 | ○ | 3 | 100 | 3 |
| 18 | ○ | 3 | ○ | 3 | ○ | 3 | 100 | 3 |

TABLE 3

| | | Human visual inspection | | | | | |
|---|---|---|---|---|---|---|---|
| Comparative example No. | Sample No. | Inspecting person A | | Inspecting person B | | Inspecting person C | |
| | | Detectability | Tact (seconds) | Detectability | Tact (seconds) | Detectability | Tact (seconds) |
| 1 | 1 | ○ | 6 | ○ | 6 | ○ | 4 |
| 2 | 2 | ○ | 5 | ○ | 6 | ○ | 6 |
| 3 | 3 | X | 7 | X | 7 | ○ | 9 |
| 4 | 4 | ○ | 9 | ○ | 8 | ○ | 7 |
| 5 | 5 | X | 8 | ○ | 7 | X | 7 |
| 6 | 6 | ○ | 9 | X | 8 | X | 9 |
| 7 | 7 | X | 6 | ○ | 5 | X | 7 |
| 8 | 8 | ○ | 6 | ○ | 6 | X | 6 |
| 9 | 9 | ○ | 5 | ○ | 5 | ○ | 4 |
| 10 | 10 | X | 7 | ○ | 8 | ○ | 9 |
| 11 | 11 | ○ | 6 | ○ | 5 | X | 6 |
| 12 | 12 | ○ | 8 | ○ | 9 | ○ | 8 |
| 13 | 13 | ○ | 6 | ○ | 6 | ○ | 6 |
| 14 | 14 | ○ | 5 | ○ | 6 | ○ | 5 |
| 15 | 15 | ○ | 6 | ○ | 5 | ○ | 6 |

| | Human visual inspection | | | | | |
|---|---|---|---|---|---|---|
| Comparative example No. | Inspecting person D | | Inspecting person E | | Detection ratio (%) | Average tact (seconds) |
| | Detectability | Tact (seconds) | Detectability | Tact (seconds) | | |
| 1 | ○ | 6 | ○ | 4 | 100 | 5 |
| 2 | ○ | 6 | ○ | 5 | 100 | 6 |
| 3 | X | 7 | X | 7 | 20 | 7 |
| 4 | ○ | 9 | ○ | 9 | 100 | 8 |
| 5 | ○ | 7 | ○ | 6 | 60 | 7 |
| 6 | ○ | 8 | X | 7 | 40 | 8 |
| 7 | ○ | 5 | X | 7 | 40 | 6 |
| 8 | ○ | 6 | X | 6 | 60 | 6 |
| 9 | ○ | 5 | ○ | 4 | 100 | 5 |
| 10 | X | 7 | ○ | 8 | 60 | 8 |
| 11 | ○ | 6 | X | 6 | 60 | 6 |
| 12 | ○ | 9 | ○ | 8 | 100 | 8 |
| 13 | ○ | 7 | ○ | 6 | 100 | 6 |
| 14 | ○ | 6 | ○ | 6 | 100 | 6 |
| 15 | ○ | 5 | ○ | 5 | 100 | 5 |

As shown in Table 2, in Examples 1 to 18 in which the inspection was performed by the inspection method of the present invention, the tact time was constantly three seconds, and the detection ratio was 100%. On the other hand, as shown in Table 3, in Comparative Examples 1 to 15 in which the inspection was performed by a human visual method, the tact time was four to nine seconds, and thus largely fluctuated owing to the inspecting persons, the dimensions of the honeycomb structure bodies and the like, and the defect was missed in not a few cases. It has been seen that it is difficult to perform stable inspection. It is to be noted that in the above examples, the sintered honeycomb structure bodies made of cordierite were used as the inspection targets. However, the inspection method of the present invention is applicable to a formed body, a dried body, a calcined body and the like as long as they are honeycomb structure bodies made of a ceramic material.

INDUSTRIAL APPLICABILITY

The present invention can preferably be used as an inspection method for detecting a defect in the outer wall of a honeycomb structure body.

The invention claimed is:

1. A method of inspecting an outer wall of a honeycomb structure body made of a ceramic material, comprising: imaging the outer wall of the honeycomb structure body by a line camera while rotating the honeycomb structure body, wherein the eccentricity of the honeycomb structure body during the rotation is within ±1.5 mm; and processing the obtained image to judge whether or not a defect is present in the outer wall of the honeycomb structure body.

2. The method of inspecting the outer wall of the honeycomb structure body according to claim 1, wherein the outer wall of the honeycomb structure body is imaged while irradiating the outer wall of the honeycomb structure body with light.

3. The method of inspecting the outer wall of the honeycomb structure body according to claim 2, wherein in a case where the honeycomb structure body is viewed from the axial direction of the honeycomb structure body, an angle at which the outer wall of the honeycomb structure body is irradiated with the light is 30° or less with respect to an axial line connecting the center of the honeycomb structure body to the line camera.

4. The method of inspecting the outer wall of the honeycomb structure body according to claim 1, including a step of binarizing the obtained image; a step of removing noise; and a step of judging whether or not the defect is present.

* * * * *